United States Patent [19]

Frey et al.

[11] Patent Number: 4,800,639
[45] Date of Patent: Jan. 31, 1989

[54] METHOD OF MAKING A METAL BONE IMPLANT

[75] Inventors: Otto Frey; Manfred Semlitsch, both of Winterthur, Switzerland

[73] Assignee: Sulzer Brothers Limited, Winterthur, Switzerland

[21] Appl. No.: 62,894

[22] Filed: Jun. 12, 1987

Related U.S. Application Data

[62] Division of Ser. No. 823,390, Jan. 28, 1986, Pat. No. 4,752,295.

[30] Foreign Application Priority Data

Feb. 7, 1985 [CH] Switzerland ............................ 559/85

[51] Int. Cl.$^4$ ............................................. B23P 17/00
[52] U.S. Cl. ...................................... 29/421.1; 29/445; 228/157
[58] Field of Search ................ 29/421 R, 445; 72/61, 72/62; 128/92 VV, 92 YL; 228/157; 623/16, 22, 23, 66

[56] References Cited

U.S. PATENT DOCUMENTS

| 1,884,589 | 10/1932 | Davies | 29/421 |
| 3,807,009 | 4/1974 | Östbo | 29/421 R X |
| 3,953,899 | 5/1976 | Charnley | 623/20 |
| 4,562,598 | 1/1986 | Kranz | 623/22 X |
| 4,718,914 | 1/1988 | Frey et al. | 623/23 |
| 4,718,916 | 1/1988 | Morscher | 623/23 |

FOREIGN PATENT DOCUMENTS

| 172262 | 11/1983 | European Pat. Off. | |
| 3417923 | 11/1985 | Fed. Rep. of Germany | 623/66 |
| 3522196 | 2/1986 | Fed. Rep. of Germany | 623/22 |
| 80495 | 3/1963 | France | 623/23 |
| 49-7789 | 2/1974 | Japan | 72/61 |

Primary Examiner—Timothy V. Eley
Assistant Examiner—Andrew E. Rawlins
Attorney, Agent, or Firm—Kenyon & Kenyon

[57] ABSTRACT

The metal bone implant is constructed with thin sheets of superplastic material which are deformed into irregular contours. The sheets are welded to the solid base element of the implant and thereafter deformed outwardly under fluid presure to an irregular shape.

7 Claims, 1 Drawing Sheet

METHOD OF MAKING A METAL BONE IMPLANT

This is a division of application Ser. No. 823,390 filed Jan. 28, 1986, now U.S. Pat. No. 4,752,295 issued June 21, 1988.

This invention relates to a metal bone implant. More particularly, this invention relates to a joint endoprosthesis having an irregular geometric shape.

As is known, in order to save weight, especially in joint endoprosthesis, such prosthesis have been made at least in part with closed cavities, such as described in French Pat. No. 2,021,313. As in the case of solid prosthesis parts, the hollow parts have heretofore been made of forged and/or cast parts which are subsequently welded together in order to form a closed hollow body. One example of such a construction is described in European patent application No. 172262 wherein a joint head for a femur head prosthesis is formed of a hollow ball of cast material and of a sleeve of forged material which is welded to the hollow ball. However, the production and machining of these previously known prosthesis, particularly where an anchoring shank with a structure consisting of ribs is involved, has been expensive and complicated.

Bone implants have also been known, for example from European patent application No. 0115564 which are made of sheet metal. In these cases, the implants have been constructed as a plug-in sleeve in order to surround an anchoring shank of a minor joint, for example made of plastic. In these cases, the form of a plug-in sleeve is relatively simple so that the production of the implant generally requires no great expense and presents no difficulties. However, there is a reduction in mechanical strength of the implant as compared with those prosthesis which are formed of individual forged and cast parts.

Accordingly, it is an object of the invention to provide a metal bone implant having a hollow construction with good mechanical properties.

It is another object of the invention to provide a relatively simple technique for forming a metal bone implant with a hollow cavity.

It is another object of the invention to provide a metal bone implant of reduced weight and good mechanical properties.

Briefly, the invention provides a metal bone implant which is comprised of a metal base element and at least two sheet metal walls which are secured to the base element in order to define a hollow body of irregular geometric shape. Preferably the walls are made of a superplastic material such as alpha/beta titanium alloy and are of thin construction, for example having a thickness of at least one millimeter.

The invention also provides a method of making a hollow implant with an irregular shape and contour. The method includes the steps of securing at least one sheet metal plate on a metal base element and thereafter deforming the sheet metal plate outwardly of the base element in a mold in order to define a hollow cavity and an irregular surface thereon. Any suitable technique may be used for the final shaping of the thin sheet metal plate. Thus, even complicated exterior forms can be easily and simply made without requiring subsequent mechanical treatments.

The invention thus provides a metal bone implant which, being made of at least part hollow construction, provides a weight reduction as compared with similar solid constructions.

The walls which define the hollow portion of the implant may be such as to provide either open or closed hollow bodies. If the walls define a closed hollow body, the cavities may be filled with light weight materials of high rigidity, for example plastic foams such as polyethylene and the like or with an elastic or plastically deformable material of stable volume, such as silicone rubber or epoxy resin. Such filling serves to increase the strength and form stability of the walls.

The stability of the walls in the final form can be increased if the form is created by at least two sheets which are disposed one on the other in layer fashion. In this case, the outer sheet which should, as closely as possible, match the form and surface of the bone wall into which the implant is to be implanted may be thinner and easier to deform than the inner sheet which essentially constitutes only a support for the outer sheet.

These and other objects and advantages of the invention will become more apparent from the following detailed description taken in conjunction with the accompany drawings wherein.

Figure 1:
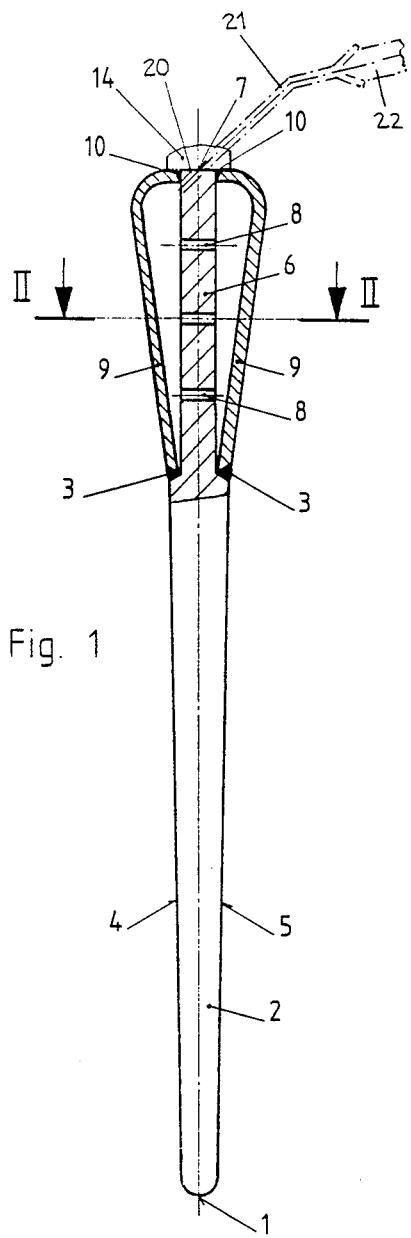
FIG. 1 illustrates a partial cross sectional view of a hip joint prosthesis constructed in accordance with the invention.

Referring to FIG. 1, the metal bone implant is in the form of a femur head prosthesis which has a straight shank 2 which flares conically from a distal end 1 towards a proximal end. As indicated, the conically flaring transverse sides 4, 5 of the shank 2 extend to a shoulder 3 and terminate in a plate-like base element 6 which extends to the proximal end 7. In addition, an enlarged prosthesis neck inception 14 is disposed at the proximal end 7 and is spatially offset against the end 7.

The base element 6 is provided with discontinuities in the form of bores 8.

In addition, the implant has a pair of sheet metal walls formed of metal sheets 9 which give form and surface to the proximal shank part. These sheets 9 also define a hollow body of irregular geometric shape within which the base element 6 is disposed. These sheets 9 may consist of a superplastic material such as an alpha/beta titanium alloy of type Ti-6Al-4v. As indicated, the lower ends of each sheet 9 are welded to the shoulder 3 of the base element while the upper ends are welded under the neck inception 14. Initially, the sheets are flat when welded to the base element 6 as indicated in FIG. 2a and are thereafter deformed into an irregular geometric shape as indicated in FIG. 2b.

Figure 2A:
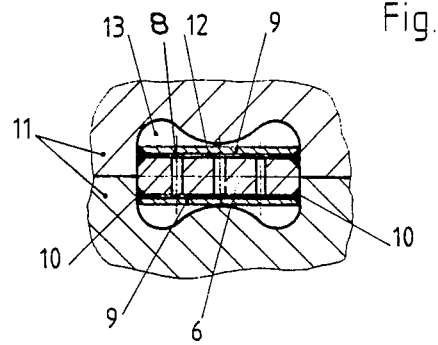
FIG. 2a illustrates an unshaped cross-section of the shank of FIG. 1 taken at the level of the section II—II.

In order to make the implant, the sheets 9 are first connected in gas tight manner with the base element 6 on the entire circumference by means of the welds 1 at the shoulder 3 and weld seams 10 which extend about the remaining periphery of the sheets 9 as indicated in FIG. 2a. Next, the proximal region of the shank 2 covered by the sheets 9 is placed in a two-part hollow mold 11, the cavity of which corresponds to the negative shape of the final form of the shank 2. Thereafter a fluid pressure medium is forced via conduits and connections into a cavity 12 between the base element 6 and the sheets 9.

To this end, as indicated in FIG. 1, a bore 20 which is shown schematically and marked in dash-dot line, penetrates the base element 6 from the proximal end and terminates in cavity 12 while a conduit 21 which leads form a source 22 of fluid pressure medium is connected to the bore 20 in order to deliver the fluid pressure medium. This causes an outward deformation of the sheets 9 from the base element 6 since the cavity 12 is impermeable to the pressure medium so that the sheets 9 assume the shape of the limiting walls of the mold cavity 13. After disconnecting the conduit 21, the bore 20 is closed by a plug, for example of welding material such as the material used to form the welds at the shoulders 3 and the seams 10.

Figure 2B:
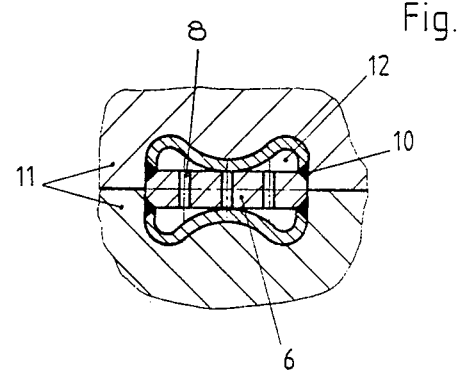
FIG. 2b illustrates a shaped cross-section of the shank of FIG. 1 at the level of section II—II.

As indicated in FIG. 2b, the bores 8 within the base element 6 permit the pressure medium to communicate with both sides of the base element 6.

Figure 3:
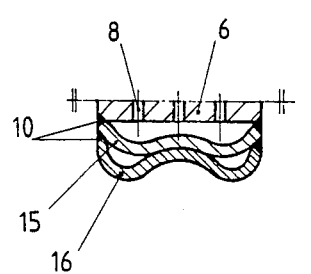
FIG. 3 illustrates a transverse section of a shank having a sheet metal wall formed of two sheets of layered construction.

Referring to FIG. 3, each wall of the implant may be formed of two sheets 15, 16 which are disposed on one another in layer fashion. In this case, the sheets are made with different deformation resistances. For example, the outer sheet 16 which is easier to deform than the inner sheet, and hence often thinner, serves to adapt the implant formed to the bone cavity. The inner sheet 15 then has the function in increase the stability of the outer sheet.

As indicated, the inner sheet 15 is welded to the base element 6 while the outer sheet 16 is welded to the inner sheet 15. In other constructions, the outer sheet 16 may completely embrace the inner sheet 15 and likewise be secured to the base element 6 directly.

The shaping of the layered sheets 15, 16 can be carried out, for example in the manner described above, and if necessary, passage openings for the pressure medium (not shown) may be present in the inner sheet 15.

The invention thus provides a metal bone implant of at least part hollow construction which has relatively good mechanical properties while providing reduced weight.

Further, the invention provides a metal bone implant wherein the outer contour of the implant can be readily shaped into an irregular contour for implantation in a bone cavity of like contour.

The use of thin sheets for the shaping of the portions of complicated form of the bone implant simplifies production and lowers the manufacturing cost noteably.

What is claimed is:

1. A method of making a bone implant comprising the steps of
    securing at least two sheet metal plates on a proximal end of a metal base element leaving a distal end of the metal base element exposed; and
    deforming each sheet metal plate outwardly of said base element in a mold to form a hollow cavity therebetween and an irregular surface on the plates.

2. A method as set forth in claim 1 wherein said step of deforming the plates includes forcing a fluid pressure medium between the base element and the plates to deform the plates.

3. A method as set forth in claim 1 which includes the steps of securing two sheet metal plates on opposite sides of the base element and deforming each plate outwardly of the base element.

4. A method as set forth in claim 3 wherein a fluid pressure medium is forced between each plate and the base element to deform each plate.

5. A method of making a bone implant comprising the steps of
    securing a pair of metal sheets to at least one side of a base element in a gas-tight manner; and
    forcing a fluid pressure medium between the sheets and the base element to deform the sheets outwardly of the base element to define a hollow cavity between said sheets and said base element.

6. A method as set forth in claim 5 which further includes the step of deforming the sheets against a mold having an irregular surface to deform the sheets into a corresponding irregular shape.

7. A method as set forth in claim 5 wherein the sheets are made of superplastic material and are plastically deformed.

* * * * *

UNITED STATES PATENT AND TRADEMARK OFFICE
CERTIFICATE OF CORRECTION

PATENT NO. : 4,800,639

DATED : January 31, 1989

INVENTOR(S) : OTTO FREY, ET AL.

It is certified that error appears in the above-identified patent and that said Letters Patent is hereby corrected as shown below:

```
Column 1, line 12 change "prosthesis" to -prostheses-
Column 1, line 37 change "prosthesis" to -prostheses-
Column 1, line 24 change "prosthesis" to -prostheses-
Column 2, lines 22 and 23 change "accompany" to -accompanying-
Column 3, line 7 change "form" to -from-
Column 4, line 5 change "noteably" to -notably-
```

Signed and Sealed this

Thirty-first Day of October, 1989

Attest:

DONALD J. QUIGG

*Attesting Officer*   *Commissioner of Patents and Trademarks*